US011636920B2

United States Patent
Xiong et al.

(10) Patent No.: US 11,636,920 B2
(45) Date of Patent: Apr. 25, 2023

(54) SYSTEMS AND METHODS FOR GENERATING AND TRAINING CONVOLUTIONAL NEURAL NETWORKS USING BIOLOGICAL SEQUENCES AND RELEVANCE SCORES DERIVED FROM STRUCTURAL, BIOCHEMICAL, POPULATION AND EVOLUTIONARY DATA

(71) Applicant: Deep Genomics Incorporated, Toronto (CA)

(72) Inventors: Hui Yuan Xiong, Toronto (CA); Brendan Frey, Toronto (CA)

(73) Assignee: Deep Genomics Incorporated, Toronto (CA)

( * ) Notice: Subject to any disclaimer, the term of this patent is extended or adjusted under 35 U.S.C. 154(b) by 1079 days.

(21) Appl. No.: 16/230,149

(22) Filed: Dec. 21, 2018

(65) Prior Publication Data
US 2019/0220740 A1   Jul. 18, 2019

Related U.S. Application Data

(63) Continuation of application No. PCT/CA2016/050777, filed on Jul. 4, 2016.

(51) Int. Cl.
| | | |
|---|---|---|
| G16B 20/20 | (2019.01) | |
| G06N 3/08 | (2006.01) | |
| G06N 3/04 | (2006.01) | |
| G16B 40/00 | (2019.01) | |
| G16B 20/00 | (2019.01) | |
| G16B 40/20 | (2019.01) | |
| G16B 30/00 | (2019.01) | |
| G16H 10/40 | (2018.01) | |
| G16H 50/30 | (2018.01) | |
| G16H 50/70 | (2018.01) | |
| G16H 50/20 | (2018.01) | |
| G16B 5/00 | (2019.01) | |
| G16B 40/30 | (2019.01) | |
| G16B 50/20 | (2019.01) | |
| G16B 20/40 | (2019.01) | |
| G16B 20/50 | (2019.01) | |
| G06N 3/084 | (2023.01) | |
| G06N 3/082 | (2023.01) | |

(52) U.S. Cl.
CPC .......... *G16B 20/20* (2019.02); *G06N 3/0454* (2013.01); *G06N 3/08* (2013.01); *G06N 3/084* (2013.01); *G16B 5/00* (2019.02); *G16B 20/00* (2019.02); *G16B 20/40* (2019.02); *G16B 30/00* (2019.02); *G16B 40/00* (2019.02); *G16B 40/20* (2019.02); *G16B 40/30* (2019.02); *G16B 50/20* (2019.02); *G16H 10/40* (2018.01); *G16H 50/20* (2018.01); *G16H 50/30* (2018.01); *G16H 50/70* (2018.01); *G06N 3/0445* (2013.01); *G06N 3/082* (2013.01); *G16B 20/50* (2019.02)

(58) Field of Classification Search
None
See application file for complete search history.

(56) References Cited

U.S. PATENT DOCUMENTS

| | | | |
|---|---|---|---|
| 9,373,059 B1 | 6/2016 | Heifets et al. | |
| 2009/0216696 A1* | 8/2009 | Downs | G06F 16/355 |
| | | | 706/20 |

FOREIGN PATENT DOCUMENTS

| | | |
|---|---|---|
| CN | 104599262 A | 5/2015 |
| CN | 105005714 A | 10/2015 |
| WO | WO-2012155148 A2 | 11/2012 |
| WO | WO-2018006152 | 1/2018 |

OTHER PUBLICATIONS

Jaderberg et al. Speeding up Convolutional Neural Networks with Low Rank Expansions arXiv:1405.3866v1 [cs.CV] (Year: 2014).*
Zhou et al. Predicting effects of noncoding variants with deep learning-based sequence model Nature Methods vol. 12 pp. 931-934 and online methods and supplementary figures (Year: 2015).*
Examination Report issued in European Application No. 16907692.4 dated Dec. 2, 2021.
Yan S et al. Prediction of mutation positions in H5N1 neuraminidases from influenza A virus by means of neural network. Ann Biomed Eng. Mar. 2010;38(3):984-92.
EP16907692.4 The Extended European Search Report dated Mar. 11, 2020.
Pajapakse, et al. Markov encoding for detecting signals in genomic sequences. IEEE/ACM Transactions on Computational Biology and Bioinformatics 2.2 (2005): 131-142.

(Continued)

*Primary Examiner* — John S Brusca
(74) *Attorney, Agent, or Firm* — Wilson Sonsini Goodrich & Rosati

(57) ABSTRACT

We describe systems and methods for generating and training convolutional neural networks using biological sequences and relevance scores derived from structural, biochemical, population and evolutionary data. The convolutional neural networks take as input biological sequences and additional information and output molecular phenotypes. Biological sequences may include DNA, RNA and protein sequences. Molecular phenotypes may include protein-DNA interactions, protein-RNA interactions, protein-protein interactions, splicing patterns, polyadenylation patterns, and microRNA-RNA interactions, which may be described using numerical, categorical or ordinal attributes. Intermediate layers of the convolutional neural networks are weighted using relevance score sequences, for example, conservation tracks. The resulting molecular phenotype convolutional neural networks may be used in genetic testing, to identify drug targets, to identify patients that respond similarly to a drug, to ascertain health risks, or to connect patients that have similar molecular phenotypes.

32 Claims, 4 Drawing Sheets

(56) References Cited

OTHER PUBLICATIONS

PCT/CA2016/050777 International Search Report dated Mar. 16, 2017.
Examination Report issued in Canadian Patent Application No. 3,030,453 dated May 16, 2022.

* cited by examiner

SYSTEMS AND METHODS FOR GENERATING AND TRAINING CONVOLUTIONAL NEURAL NETWORKS USING BIOLOGICAL SEQUENCES AND RELEVANCE SCORES DERIVED FROM STRUCTURAL, BIOCHEMICAL, POPULATION AND EVOLUTIONARY DATA

CROSS-REFERENCE

This application is a continuation of International Application No. PCT/CA2016/050777, filed Jul. 4, 2016, which is incorporated herein by reference in its entirety and to which application we claim priority under 35 USC § 120.

TECHNICAL FIELD

The following relates generally to generating and training a convolutional neural network for predicting molecular phenotypes from biological sequences.

BACKGROUND

Precision medicine, genetic testing, therapeutic development and whole genome, exome, gene panel and mini-gene reporter analysis require the ability to accurately interpret how mutations in a biological sequence, such as a DNA, RNA or protein sequence may impact processes within cells. Molecular phenotypes, also know as cell variables, are measurable outcomes of processes that are carried out within the cell. Examples of molecular phenotypes include protein-DNA and protein-RNA binding, chromatin state, transcription, RNA splicing, polyadenylation, RNA editing, translation, protein-protein interaction, and postranscriptional modification.

Molecular phenotypes are often causally determined by biological sequences that are close to where they occur. For example, the existence or absence of a particular motif on a DNA sequence may determine if a particular DNA binding protein will bind. An exon on a precursor mRNA may be spliced out during RNA splicing depending on the combined effects of a set of intronic and exonic motifs of RNA-binding proteins within and around that exon. Understanding and modelling how biological sequences determine molecular phenotypes is viewed as a major set of goals in biological and medical research.

SUMMARY

In one aspect, a system for weighting convolutional layers in molecular phenotype convolutional neural networks (MPCNNs) is provided, the system comprising: at least three layers, each layer configured to receive inputs and produce outputs, a first layer comprising a plurality of positions configured to obtain a biological sequence, a last layer representing a molecular phenotype, each layer other than the first layer configured to receive inputs from the produced outputs of one or more prior layers; one or more of the at least three layers configured as convolutional layers, each convolutional layer comprising one or more convolutional filters linking received inputs in the convolutional layer to produced outputs in the convolutional layer, the received inputs in the convolutional layer comprising a plurality of convolutional layer input positions, the produced outputs in the convolutional layer comprising a plurality of convolutional layer output positions; and one or more weighting units, each weighting unit linked to at least one of the one or more convolutional filters in a convolutional layer, each weighting unit associated with a relevance score sequence, each relevance score sequence comprising a plurality of relevance score sequence positions, each relevance score sequence position associated with a numerical value, the weighting unit configured to use the respective relevance score sequence to weight the operations in the respective convolutional filter.

In at least one of the one or more weighting units, the respective relevance score sequence may be used to weight the produced outputs in the respective convolutional layer.

In at least one of the one or more weighting units, the respective relevance score sequence may be used to weight the received inputs in the respective convolutional layer.

One or more of the at least three layers may be configured as pooling layers, each pooling layer comprising a pooling unit linking received inputs in the pooling layer to produced outputs in the pooling layer, the received inputs in the pooling layer comprising a plurality of pooling layer input positions, the produced outputs in the pooling layer comprising a plurality of pooling layer output positions, the number of pooling layer output positions no greater than three quarters of the number of pooling layer input positions, the received inputs in the pooling layer linked to the produced outputs of at least one of the one or more convolutional layers.

At least one of the at least three layers other than the first layer may be configured as a fully connected layer, the produced outputs in each fully connected layer obtained by multiplying the received inputs in the fully connected layer by corresponding parameters, summing the resulting terms, and applying a linear or a nonlinear function.

The relevance score sequences may be obtained from evolutionary conservation sequences, population allele frequency sequences, nucleosome positioning sequences, RNA-secondary structure sequences, protein secondary structure sequences, and retroviral insertion sequences.

The system may further comprise an encoder configured to encode the biological sequence as a vector sequence, wherein the biological sequence with a plurality of positions in the first layer comprises the vector sequence.

The system may further comprise a MPCNN training unit and a plurality of training cases, each training case comprising a biological sequence and a molecular phenotype, the MPCNN training unit configured to adjust the filters and the other parameters in the MPCNN using one or more of: batch gradient descent, stochastic gradient descent, dropout, the conjugate gradient method.

The relevance score sequences may be the outputs of a relevance neural network comprising relevance neural network parameters, the relevance score neural network configurable as a fully connected neural network, a convolutional neural network, a multi-task neural network, a recurrent neural network, a long short-term memory neural network, an autoencoder, or a combination thereof.

The system may further comprise a relevance neural network training unit and a plurality of training cases, each training case comprising a biological sequence and a molecular phenotype, the relevance neural network training unit configured to adjust the relevance neural network parameters using the gradients for the relevance neural network parameters, the gradients for the relevance neural network parameters determined by operating the MPCNN in the forward-propagation mode to determine the error and operating the MPCNN in back-propagation mode to ascertain the gradients for the outputs of the relevance neural network and operating the relevance neural network in back-propagation mode to ascertain the gradients for the relevance neural network parameters, the relevance neural network training unit configured to adjust the parameters of the relevance neural network using one or more of: batch gradient descent, stochastic gradient descent, dropout, the conjugate gradient method.

In another aspect, a method for utilizing relevance score sequences to weight layers in molecular phenotype convolutional neural networks (MPCNNs) is provided, the method comprising: each of at least three layers receiving inputs and producing outputs, a first layer comprising a biological sequence with a plurality of positions, a last layer representing a molecular phenotype, each layer other than the first layer receiving inputs from the produced outputs of one or more prior layers, one or more of the at least three layers acting as convolutional layers, each convolutional layer comprising the application of one or more convolutional filters to the received inputs in the convolutional layer to produce outputs in the convolutional layer, the received inputs in the convolutional layer comprising a plurality of convolutional layer input positions, the produced outputs in the convolutional layer comprising a plurality of convolutional layer output positions; obtaining one or more relevance score sequences, each relevance score sequence comprising a plurality of relevance score sequence positions, each relevance score sequence position associated with a numerical value; and applying one or more weighting operations, each weighting operation using an associated relevance score sequence in the one or more relevance score sequences to weight the application of an associated convolutional filter in the application of one or more convolutional filters.

In at least one of the one or more weighting operations, the associated relevance score sequence may be used to weight the produced outputs of the associated convolutional filter.

In at least one of the one or more weighting operations, the associated relevance score sequence may be used to weight the received inputs of the associated convolutional filter.

One or more of the at least three layers may be configured as pooling layers, each pooling layer comprising a the application of a pooling operation to the received inputs in the pooling layer to produce outputs in the pooling layer, the received inputs in the pooling layer comprising a plurality of pooling layer input positions, the produced outputs in the pooling layer comprising a plurality of pooling layer output positions, the number of pooling layer output positions no greater than three quarters of the number of pooling layer input positions, the received inputs in the pooling layer obtained from the produced outputs of at least one of the one or more convolutional layers.

At least one of the at least three layers other than the first layer may be configured as a fully connected layer, the produced outputs in each fully connected layer obtained by multiplying the received inputs in the fully connected layer by corresponding parameters, summing the resulting terms, and applying a linear or a nonlinear function.

The relevance score sequences may be obtained from evolutionary conservation sequences, population allele frequency sequences, nucleosome positioning sequences, RNA-secondary structure sequences, protein secondary structure sequences, and retroviral insertion sequences.

The method may further comprise an encoding operation that encodes the biological sequence as a vector sequence, wherein the biological sequence with a plurality of positions in the first layer comprises the vector sequence.

The method may further comprise training the MPCNN using a plurality of training cases, each training case comprising a biological sequence and a molecular phenotype, the training of the MPCNN comprising adjusting the filters and the other parameters in the MPCNN using one or more of: batch gradient descent, stochastic gradient descent, dropout, the conjugate gradient method.

The relevance score sequences may be generated by a relevance neural network which may be configured as a fully connected neural network, a convolutional neural network, a multi-task neural network, a recurrent neural network, a long short-term memory neural network, an autoencoder, or a combination thereof.

The method may further comprise training the relevance neural network using a plurality of training cases, each training case comprising a biological sequence and a molecular phenotype, the training of the relevance neural network comprising: operating the MPCNN in the forward-propagation mode to determine the error; operating the MPCNN in back-propagation mode to ascertain the gradients for the outputs of the relevance neural network; operating the relevance neural network in back-propagation mode to ascertain the gradients for the relevance neural network parameters; using the gradients for the relevance neural network parameters to adjust the relevance neural network parameters using one or more of batch gradient descent, stochastic gradient descent, dropout, the conjugate gradient method.

These and other aspects are contemplated and described herein. It will be appreciated that the foregoing summary sets out representative aspects of methods and systems for producing an expanded training set for machine learning using biological sequences to assist skilled readers in understanding the following detailed description.

DESCRIPTION OF THE DRAWINGS

The features of the invention will become more apparent in the following detailed description in which reference is made to the appended drawings wherein.

DETAILED DESCRIPTION

Figure 1:
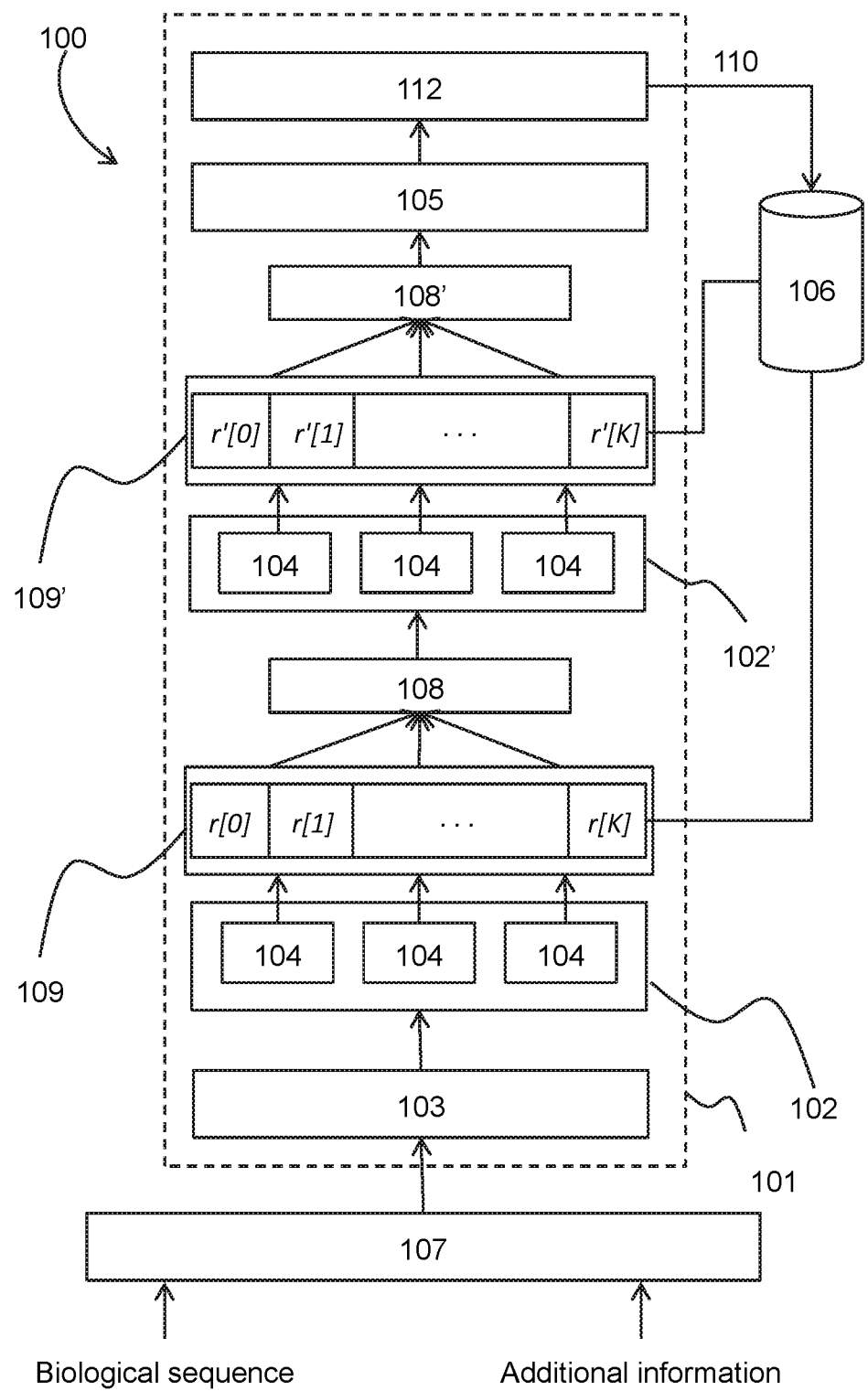
FIG. 1 is a block diagram illustrating an embodiment of a system for training convolutional neural networks using biological sequences and relevance scores.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

A key unmet need is the ability to automatically or semi-automatically analyze biological sequences by examining their impact on molecular phenotypes.

The following provides systems and methods for determining molecular phenotypes from biological sequences using convolutional neural networks, called molecular phenotype convolutional neural networks (MPCNNs). The biological sequence may be a DNA sequence, an RNA sequence, or a protein sequence. The outputs of MPCNNs may be used in precision medicine to ascertain pathogenicity in genetic testing, to identify drug targets, to identify patients that respond similarly to a drug, to ascertain health risks, and to connect patients that have similar molecular phenotypes.

Variations in biological sequences lead to changes in molecular phenotypes, which may lead to gross phenotypes, such as disease, aging, and effective treatment. A biological sequence variant, also called a variant, is a biological sequence, such as a DNA sequence, an RNA sequence or a protein sequence, that may be derived from an existing biological sequence through a combination of substitutions, insertions and deletions. For example, the gene BRCA1 is represented as a specific DNA sequence of length 81,189 in the reference genome. If the samples from multiple patients are sequenced, then multiple different versions of the DNA sequence for BRCA1 may be obtained. These sequences, together with the sequence from the reference genome, form a set of variants.

To distinguish variants that are derived from the same biological sequence from those that are derived from different biological sequences, the following will refer to variants that are derived from the same biological sequence as "biologically related variants" and the term "biologically related" is used as an adjective to imply that a variant is among a set of biologically related variants. For example, the variants derived from the gene BRCA1 are biologically related variants. The variants derived from another gene, SMN1, are also biologically related variants. However, the variants derived from BRCA1 are not biologically related to the variants derived from SMN1. The term "biologically related variants" is used to organize variants according to their function, but it will be appreciated that this organization may be different according to different functions. For example, when they are transcribed, two different but homologous genes may generate the same RNA sequence. Variants in the RNA sequence may impact function in the same way, such as by impacting RNA stability. This is the case even though they originated from two different, albeit homologous, DNA sequences. The RNA sequence variants, regardless of from which gene they came, may be considered to be biologically related.

Biologically related variants may be derived naturally by DNA replication error; by spontaneous mutagenesis; by sexual reproduction; by evolution; by DNA, RNA and protein editing/modification processes; by retroviral activity, and by other means. Biologically related variants may be derived experimentally by plasmid construction, by gene editing systems such as CRISPR/Cas9, by sequencing samples from patients and aligning them to a reference sequence, and by other means. Biologically related variants may be derived computationally by applying a series of random or preselected substitutions, insertions and deletions to a reference sequence, by using a model of mutation to generate variants, and by other means. Biologically related variants may be derived from a DNA or RNA sequence of a patient, a sequence that would result when a DNA or RNA editing system is applied, a sequence where nucleotides targeted by a therapy are set to fixed values, a sequence where nucleotides targeted by a therapy are set to values other than existing values, or a sequence where nucleotides that overlap, fully or partially, with nucleotides that are targeted by a therapy are deactivated. It will be appreciated that there are other ways in which biologically related variants may be produced.

Depending on the function being studied, different sets of biologically related variants may be obtained from the same biological sequences. In the above example, DNA sequences for the BRCA1 gene of length 81,189 may be obtained from the reference genome and a group of patients and form a set of biologically related variants. As an example, if we are interested in how variants impact splicing of exon 6 in BRCA1, for each patient and the reference genome, we may extract a subsequence of length 600 nucleotides centered at the 3 prime end of exon 6. These splice site region sequences would form a different set of biologically related variants than the set of whole-gene biologically related variants.

The above discussion underscores that the functional meaning of a variant is context dependent, that is, dependent on the conditions. Consider the reference genome and an intronic single nucleotide substitution located 100 nucleotides from the 3 prime splice site of exon 6 in the BRCA1 gene. We can view this as two BRCA1 variants of length 81,189 nucleotides, or as two exon 6 splice site region variants of length 600 nucleotides, or, in the extreme, as two chromosome 17 variants of length 83 million nucleotides (BRCA1 is located on chromosome 17). Viewing the single nucleotide substitution in these three different situations would be important for understanding its impact on BRCA1 gene expression, BRCA1 exon 6 splicing, and chromatin interactions in chromosome 17. Furthermore, consider the same single nucleotide substitution in two different patients. Because the neighbouring sequence may be different in the two patients, the variants may be different.

A variant impacts function by altering one or more molecular phenotypes, which quantify aspects of biological molecules that participate in the biochemical processes that are responsible for the development and maintenance of human cells, tissues, and organs. A molecular phenotype may be a quantity, level, potential, process outcome, or qualitative description. The term "molecular phenotype" may be used interchangeably with the term "cell variable". Examples of molecular phenotypes include the concentration of BRCA1 transcripts in a population of cells; the percentage of BRCA1 transcripts that include exon 6; chromatin contact points in chromosome 17; the strength of binding between a DNA sequence and a protein; the strength of interaction between two proteins; DNA methylation patterns; RNA folding interactions; and inter-cell signalling. A molecular phenotype can be quantified in a variety of ways, such as by using a categorical variable, a single numerical value, a vector of real-valued numbers, or a probability distribution.

A variant that alters a molecular phenotype is more likely to alter a gross phenotype, such as disease or aging, than a variant that does not alter any molecular phenotype. This is because variants generally impact gross phenotypes by altering the biochemical processes that rely on DNA, RNA and protein sequences.

Since variants impact function by altering molecular phenotypes, a set of biologically related variants can be associated with a set of molecular phenotypes. BRCA1 whole-gene variants may be associated with the molecular phenotype measuring BRCA1 transcript concentration. BRCA1 exon 6 splice site region variants may be associated with the molecular phenotype measuring the percentage of BRCA1 transcripts that include exon 6. Chromosome 17 variants may be associated with the molecular phenotype measuring chromatin contact points in chromosome 17. This association may be one to one, one to many, many to one, or many to many. For instance, BRCA1 whole-gene variants, BRCA1 exon 6 splice region variants and chromosome 17 variants may be associated with the molecular phenotype measuring BRCA1 transcript concentration.

The association of a variant with a molecular phenotype does not imply for certain that the variant alters the molecular phenotype, it only implies that it may alter the molecular phenotype. An intronic single nucleotide substitution located 100 nucleotides from the 3 prime splice site of exon 6 in the BRCA1 gene may alter the percentage of BRCA1 transcripts that include exon 6, whereas a single nucleotide substitution located 99 nucleotides from the 3 prime splice site of exon 6 in the BRCA1 gene may not. Also, for the former case, whereas a G to T substitution may alter the molecular phenotype, a G to A substitution may not. Furthermore, the molecular phenotype may be altered in one cell type, but not in another, even if the variant is exactly the same. This is another example of context dependence.

There are different approaches to determining how variants alter the same molecular phenotype, ranging from experimental, to computational, to hybrid approaches.

The present systems comprise structured computational architectures referred to herein as molecular phenotype neural networks (MPNNs). MPNNs are artificial neural networks, also called neural networks, which are a powerful class of architectures for applying a series of computations to an input so as to determine an output. The input to the MPNN is used to determine the outputs of a set of feature detectors, which are then used to determine the outputs of other feature detectors, and so on, layer by layer, until the molecular phenotype output is determined. An MPNN architecture can be thought of as a configurable set of processors configured to perform a complex computation. The configuration is normally done in a phase called training, wherein the parameters of the MPNN are configured so as to maximize the computation's performance on determining molecular phenotypes or, equivalently, to minimize the errors made on that task. Because the MPNN gets better at a given task throughout training, the MPNN is said to be learning the task as training proceeds. MPNNs can be trained using machine learning methods. Once configured, an MPNN can be deployed for use in the task for which it was trained and herein for linking variants as described below.

A neural network architecture can be thought of as a configurable computation. The configuration is normally done in a phase called training, wherein the parameters of the neural network are configured so as to maximize the computation's performance on a particular task or, equivalently, to minimize the errors made on that task. Because the neural network gets better at a given task throughout training, the network is said to be learning the task as training proceeds. Neural networks can be trained using machine learning techniques. Once configured, a neural network can be deployed for use in the task for which it was trained.

Fully connected neural networks are comprised of layers of feature detectors. The layers are ordered. The first layer is an input layer into which the inputs to the neural network are loaded. For example, the input layer may obtain a biological sequence represented as a vector sequence and additional information. The last layer is the output layer, for example, the molecular phenotype. In a fully connected neural network, each feature detector in each layer of feature detectors receives input from all of the feature detectors in the previous layer.

The systems and methods described herein make use MPNNs that are configured as a class of neural networks called convolutional neural networks. These are referred to as molecular phenotype convolutional neural networks (MPCNNs).

MPCNNs may be constructed to account for the relationships between biological sequences and molecular phenotypes that they may influence. Machine learning methods may be used to construct these computational models by extracting information from a dataset comprising measured molecular phenotypes, DNA, RNA or protein sequences.

MPCNNs operate by: applying a set of convolutional filters (arranged as one or more convolutional layers) to the input sequence; applying non-linear activation functions to the outputs of the convolutional filters; and applying a pooling operation to the output of these activation functions (also known as pooling layers) to obtain a feature map. These three steps may be applied, recursively, to the feature map, by replacing the input sequence with the feature map, to obtain deeper feature maps. This may be repeated to obtain even deeper feature maps, and so on. At some point the output is obtained by applying a non-convolutional neural network to the deepest feature map.

The convolutional filters in MPCNNs are shared across sequence positions and act as sequence feature detectors. The non-linear activation functions identify significant filter responses while repressing spurious responses caused by insufficient and often idiosyncratic matches between the filters and the input sequences. The pooling procedure detects the occurrence of sequence features within a spatial window, providing a certain translational invariance to the MPCNN. The fully connected network combines information across different feature detectors to make a prediction.

It will be appreciated that there are different variations of convolutional neural networks, including extensions such as recursive neural networks, that the systems and methods described herein may make use of.

While MPCNNs have been used to determine molecular phenotypes, such as protein-DNA binding, an important weakness of those CNNs is the presence of activations within feature maps in regions where activity should not be present. This leads to the inaccurate ascertaining of molecular phenotypes.

This occurs because these MPCNNs assume that each filter should be applied equally in all regions of the input, that is, everywhere in the biological sequence. However, biological sequences often have complex structures that vary across the sequence and these structures impact the accuracy and utility of detected features. For instance, a nucleosome may block certain DNA sequence elements from having function. As a result, treating all positions in a biological sequence in the same way when applying convolutional filters can be suboptimal.

Applying convolutional filters to biological sequences, such as DNA, RNA, or protein sequences, naively assumes that positions within the biological sequences respond in a uniform way to the convolutional filters which may result in spurious firing of feature detectors and may in turn result in suboptimal predictive performance of the MPCNN. Applicant has determined that the main cause of this phenomenon is that particular positions within the biological sequence may not be relevant for a particular convolutional filter or sequence feature detector. For example, a position in an RNA molecule might be folded into a stem in a stem-and-loop secondary structure. In the secondary structure, certain positions are paired with some other RNA sequences, making them inaccessible to RNA-binding proteins that only bind to single-stranded RNA. As a result, the motif detector of the forgoing RNA-binding proteins should ideally be suppressed for those positions within a paired secondary structure. Instead of naïvely scanning the RNA sequence with the motif, leveraging information of secondary structure may improve the specificity of the activation of motif detectors and may improve overall predictive performance of the system.

Systems and methods are provided herein for training convolutional neural networks using biological sequences along with relevance scores derived from structural, biochemical, population and evolutionary data. The relevance scores are position- and filter-specific to suppress undesirable detected features and make the MPCNN more effective. The relevance scores can be provided to the MPCNN as a relevance score sequence. As will be described herein, in various embodiments the relevance scores may be determined using a separate neural network, referred to herein as a relevance neural network, which may be trained concurrently with the training of the MPCNN, or separately.

It will be appreciated that the biological sequence may be a variant of another biological sequence, and may be experimentally determined, derived from an experimentally determined sequence, arise due to evolution, due to spontaneous mutations, due to gene editing, or be determined in another way.

Referring now to FIG. 1, a system (100) in accordance with the foregoing comprises a MPCNN (101) that is a convolutional neural network comprising a layer of input values (103) that represents a biological sequence (which may be referred to as an "input layer"), at least one alternating set of convolutional and pooling layers comprising one or more convolutional layers (102,102') each comprising one or more convolutional filters (104) and one or more pooling layers (108, 108'), and a neural network (105), the output of which provides output values (110) that represent the computed relevance scores (which may be referred to as an "output layer" (112)).

Each convolutional filter (104) implements a feature detector, wherein each feature detector comprises or is implemented by a processor. The relevance score for each position of a biological sequence are stored in a memory (106) and linked to a weighting unit (109). Weights may be applied in each convolutional feature detector (104) in accordance with learned weighting. Non-linear activation functions are applied to the convolutional filters, and the pooling layers (108) apply a pooling operation to the output of these activation functions.

The particular MPCNN (101) shown in FIG. 1 is an example architecture; the particular links between the convolutional feature detectors (104) and the pooling layers (108) may differ in various embodiments, which are not all depicted in the figures. The neural network (105) may be omitted and each pooling layer (108, 108') may be omitted or configured to pool differently. A person of skill in the art would appreciate that such embodiments are contemplated herein.

As shown in the system depicted in FIG. 1, the input to the MPCNN comprises a biological sequence encoded by an encoder (107) as a vector sequence. It will be appreciated that the input may include additional information, which may comprise, for example, environmental factors, cell labels, tissue labels, disease labels, and other relevant inputs.

One method that may be applied by the encoder (107) is to encode the sequence of symbols in a sequence of numerical vectors, a vector sequence, using, for example, one-hot encoding. The symbol $s_i$ is encoded in a numerical vector $x_i$ of length m: $x_i=(x_{i,1}, \ldots, x_{i,m})$ where $x_{i,j}=[s_i=\alpha_j]$ and [•] is defined such that [True]=1 and [False]=0 (so called Iverson's notation). One-hot encoding of all of the biological sequence elements produces an m×n matrix X. For example, a DNA sequence CAAGTTT of length n=7 and with an alphabet $\mathcal{A}=(A, C, G, T)$, such that m=4, would produce the following vector sequence:

$$X = \begin{pmatrix} 0 & 1 & 1 & 0 & 0 & 0 & 0 \\ 1 & 0 & 0 & 0 & 0 & 0 & 0 \\ 0 & 0 & 0 & 1 & 0 & 0 & 0 \\ 0 & 0 & 0 & 0 & 1 & 1 & 1 \end{pmatrix}.$$

Such an encoding is useful for representing biological sequences as numeric inputs to the neural network. It will be appreciated that other encodings of X may be computed from linear or non-linear transformations of a one-hot encoding, so long as the transformed values are still distinct.

The MPCNN examples described above may all be implemented by the same or possibly different MPCNN structures; that is, the number, composition and parameters of the filters, layers and pooling may or may not differ. It will be appreciated that the biological sequences need not be of the same length and that an MPCNN may be trained to account for other molecular phenotypes, for other biologically related variants and for other specifications of the additional information.

It will also be appreciated that many different machine learning architectures can be represented as neural networks, including linear regression, logistic regression, softmax regression, decision trees, random forests, support vector machines and ensemble models. Differences between techniques and architectures often pertain to differences in the cost functions and optimization procedures used to configure the architecture using a training set.

It will also be appreciated that the MPCNN may also take as input a vector of features that are derived from the variant sequence. Examples of features include locations of protein binding sites, RNA secondary structures, chromatin interactions, and protein structure information.

In the MPCNN (101), the output of the convolutional layers are affected by relevance score sequences which are implemented in a weighting unit (109). The relevance score sequences are derived from structural, biochemical, population, or evolutionary data. The relevance score sequences signify how relevant each position of a biological sequence is with respect to each convolutional filter. In one aspect, each relevance score in a relevance score sequence is used to scale the effect of the corresponding position within a biological sequence with respect to a convolutional filter.

The relevance scores affect the output of the convolutional filters with the effect of a soft mask on the activations of the convolutional feature detector in regions that are not capable of interacting with the biological process. The relevance score may, for example, be a number between zero and one, where zero indicates minimal relevance and one indicates maximal relevance. In another embodiment, the relevance scores can have unbounded values and can be interpreted as how the response of each position should be scaled for each convolutional filter.

The relevance score for each position of a biological sequence is stored in the memory (106) and input to the weighting unit (109). In the embodiment shown in FIG. 1, the weighting unit (109, 109') is applied at the output of each convolutional filter (104) that is designed to be the result of a convolution weighted by the relevance score. Denote the output of one of the convolutional filters by y and denote the i th output of the filter by y[i]. It is set as follows:

$$y[i] \leftarrow r[i] \sum_{k=-K}^{K} s[i-k]h[k],$$

where '←' is the operation of using a computational architecture implementing the formula to the right of the arrow and storing it in a memory location represented by the symbol to the left of the arrow. Here, h[k] represents the convolutional filter component at the k th position, s[i] represents the symbol at position i in the biological sequence (103) or the output of the previous pooling layer (108), and r[i] is the relevance score at position i. At other layers, the same or different relevance score sequences may be used, such as r' at (109'). It will be appreciated that the convolution operation may be computed using multiple processors or threads in a multi-threaded machine and that there are other ways of implementing the convolution operation to achieve a similar effect.

It will be appreciated that the sequence at the output of the convolutional filter (104) may be shorter than the sequence that is input to the convolutional filter, because of the application of the filter. It will be appreciated that the output sequence may be the same size as the input sequence, which may be achieved using zero padding, if the input sequence is analyzed with wrap-around.

Since the pooling operation results in shorter sequences, the relevance score sequences that are applied after pooling may be shorter than those applied before pooling. For example, in FIG. 1, if the pooling layer (108) reduces the length of the sequence by one half, then the relevance score sequence r' applied at (102') would be half as long as the relevance score sequence r applied at (102).

Both s[i] and h[k] may be vectors that encode a symbol from a discrete alphabet. For example, if the biological sequence is a DNA sequence, s[i]=(1, 0, 0, 0) encodes the nucleotide A, s[i]=(0, 1, 0, 0) encodes the nucleotide C, s[i]=(0, 0, 1, 0) encodes the nucleotide G, and s[i]=(0, 0, 0, 1) encodes the nucleotide T. Similarly for this example, h[k] is a vector with four dimensions. The operation s[i−k]h[k] is a dot product between the two vectors.

Figure 2:
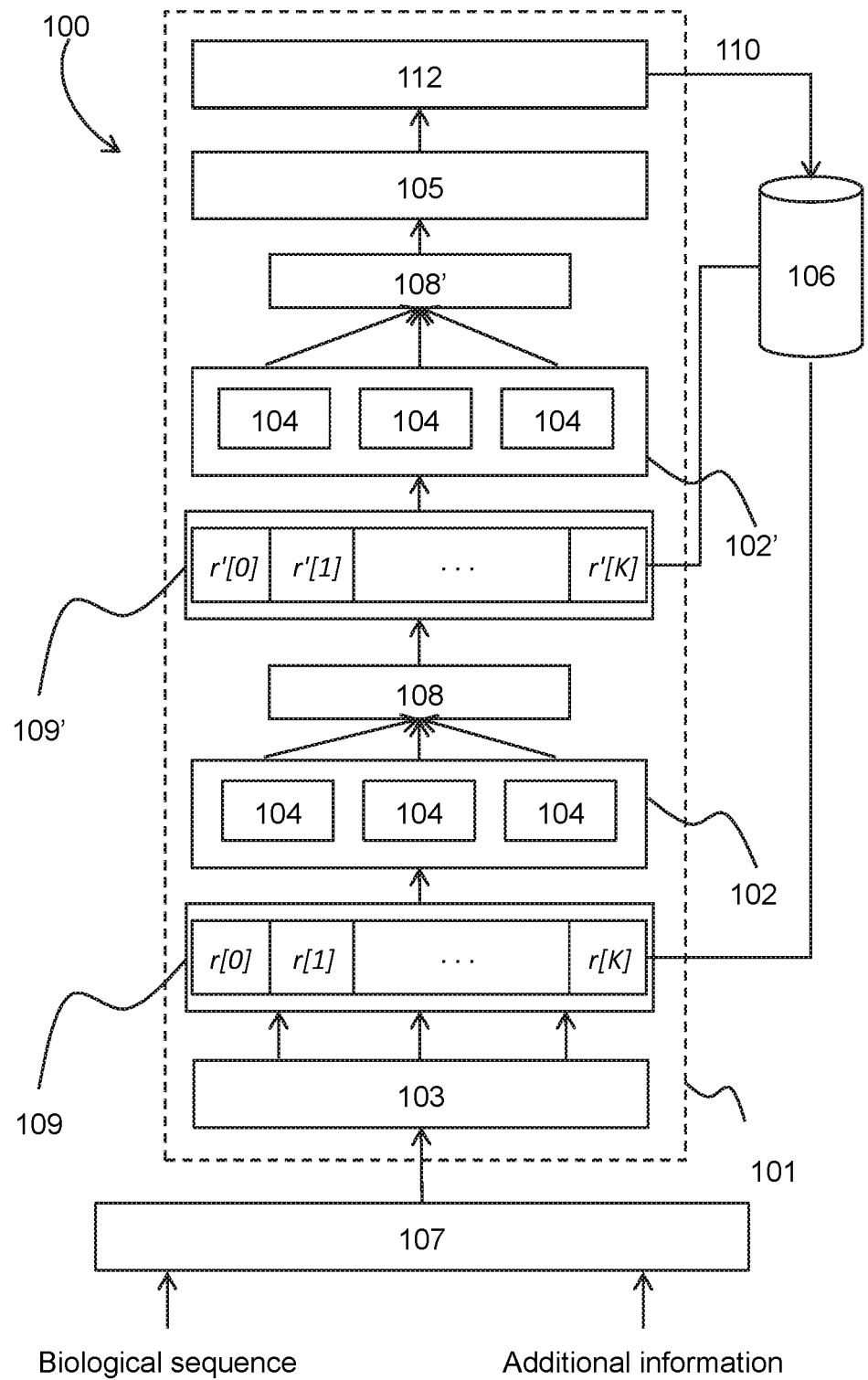
FIG. 2 shows an example flowchart of how the relevance scores may be determined using the methods and systems described herein.

In another embodiment, as shown in FIG. 2, the input sequences to the convolutional filters (104) are weighted by the weighting unit (109) before the convolution occurs:

$$y[i] \leftarrow \sum_{k=-K}^{K} r[i-k]s[i-k]h[k].$$

The weighting unit (109) may alternatively implement a different weighting for the output of the convolutional filters (104). For example, an alternative setting of the i th output of the filter, y[i], sets input sequence elements that are less relevant to be closer to a reference vector m that describes a reference encoding:

$$y[i] \leftarrow \sum_{k=-K}^{K} (r[i-k]s[i-k] + (1 - r[i-k])m)h[k].$$

The reference vector corresponds to an average sequence. For example, for a DNA sequence, the reference vector, m, is a four dimensional vector, m=($m_1$, $m_2$, $m_3$, $m_4$), and a particular choice would be m=(0.25,0.25,0.25,0.25).

It will be appreciated that the architectures implementing the above computations can be structured in different ways to achieve the same or a similar effect. For instance the computation:

$$y[i] \leftarrow \sum_{k=-K}^{K} (r[i-k]s[i-k] + (1 - r[i-k])m)h[k]$$

can be implemented as follows. Because different filters are applied to the same relevance-weighted sequences, it can be efficient to first compute the following:

$$a[i] \leftarrow r[i]s[i],$$

$$b[i] = (1-r[i])m,$$

$$c[i] \leftarrow a[i]+b[i].$$

Next, for a given convolution filter h[k], the filter output can be computed using the architecture:

$$y[i] \leftarrow \sum_{k=-K}^{K} c[i-k]h[k]$$

In another aspect, the relevance score is a scalar numerical value for each position and for each filter. For J filters $h_1[k]$, $h_2[k]$, ... $h_J[k]$, there are J relevance score sequences $r_1[i]$, $r_2[i]$, ... $r_J[i]$, and in one embodiment the J filter outputs are:

$$y_j[i] \leftarrow \sum_{k=-K}^{K} r_j[i-k]s[i-k]h_j[k].$$

It will be appreciated that the different embodiments described above can make use of these filter-specific relevance scores.

In one embodiment, the MPCNN may be trained by operating the MPCNN in a modified back-propagation mode using a dataset of examples, wherein each example comprises a biological sequence; a relevance score sequence; and targets corresponding to the outputs of the MPCNN. For each example, the MPCNN is operated in the forward-propagation mode to ascertain the outputs of the MPCNN. Then, the MPCNN is operated in a modified back-propagation mode to determine the gradients for the parameters. These gradients are collected over examples, such as batches or minibatches, and are used to update the parameters. It will be appreciated that for all of the embodiments described above, the filter output can be differentiated with respect to the parameters of the filters. The resulting gradients can be viewed as gradients determined using a standard MPCNN, but weighted using the relevance scores.

In the embodiment wherein the filter output is $$y[i] \leftarrow r[i] \sum_{k=-K}^{K} s[i-k]h[k],$$

the gradient of the filter output y[i] with respect to the filter value h[k'] is given by $$\left(\frac{\partial y[i]}{\partial h[k']}\right)^{mod} \leftarrow r[i]s[i-k'].$$

In the regular back-propagation procedure, wherein the relevance score is unity, the gradient is $$\left(\frac{\partial y[i]}{\partial h[k']}\right)^{reg} \leftarrow s[i-k'].$$

So, the modified backpropagation procedure computes gradients that are related to the gradients computed in the regular back-propagation procedure as follows:

$$\left(\frac{\partial y[i]}{\partial h[k']}\right)^{mod} \leftarrow r[i]\left(\frac{\partial y[i]}{\partial h[k']}\right)^{reg}.$$

In the embodiment wherein the filter output is $$y_j[i] \leftarrow \sum_{k=-K}^{K} r_j[i-k]s[i-k]h_j[k],$$

the gradient of the filter output $y_j[i]$ with respect to the filter value $h_j[k']$ as determined by the modified back-propagation procedure is given by $$\left(\frac{\partial y_j[i]}{\partial h_j[k']}\right)^{mod} \leftarrow r_j[i-k']s[i-k'].$$

The regular back-propagation procedure results in the gradient, $$\left(\frac{\partial y_j[i]}{\partial h_j[k']}\right)^{reg} \leftarrow s[i-k'],$$

so that the modified gradient is related to the regular gradient as follows:

$$\left(\frac{\partial y_j[i]}{\partial h_j[k']}\right)^{mod} \leftarrow r_j[i-k']\left(\frac{\partial y_j[i]}{\partial h_j[k']}\right)^{reg}.$$

It will be appreciated that these derivatives may be computed by modifying the back-propagation architecture used to train the MPCNN in different ways.

In another aspect, the relevance score sequences may be applied not only to the lowest level convolutional filters that act on biological sequences, but also to intermediate-level convolutional filters that act on feature maps generated by lower-level convolutional filters. These implementations are shown in FIG. 1 and FIG. 2, wherein a plurality of weighting units (109 and 109') are shown. These intermediate-level convolutional filters (102') may detect intermediate-level biological sequence features and have a receptive field with a size that depends on the size of the lower level convolutional filters and pooling layers. The derivatives describe above can be used in intermediate layers to compute the derivatives for intermediate-layer filters. Back-propagation will require the derivatives of the inputs to the convolutional operation. It will be appreciated that these derivatives can be computed and incorporated into the architecture used for back-propagation in the MPCNN.

Let $y^l[i]$ be the filter activation at position i in layer l of the MPCNN, that $s^{l-1}[i]$ is the pooled activity of the previous layer l-1 in the MPCNN, that $h^l[k]$ is a filter applied at layer l, and $r^l[i]$ is the relevance score at position i for the intermediate layer, so that during forward-propagation, $$y^l[i] \leftarrow r^l[i] \sum_{k=-K}^{K} s^{l-1}[i-k]h^l[k].$$

Back-propagation makes use of the gradient of the filter output with respect to the pooled activity from the previous layer:

$$\left(\frac{\partial y^l[i]}{\partial s^{l-1}[i']}\right)^{mod} \leftarrow r^l[i]s^{l-1}[i']h^l[i-i'],$$

for $|i-i'|\leq K$ and zero otherwise. In this embodiment the modified gradients are related to the regular gradients as follows:

$$\left(\frac{\partial y^l[i]}{\partial s^{l-1}[i']}\right)^{mod} \leftarrow r^l[i]\left(\frac{\partial y^l[i]}{\partial s^{l-1}[i']}\right)^{reg}.$$

It will be appreciated that the modified gradients can be determined from the formula for the regular gradients for other architectures in a similar manner.

In another embodiment, the relevance scores may be determined using neural networks whose inputs comprise position-dependent tracks obtained with structural, biochemical, population and evolutionary data of biological sequences. The neural networks have configurable parameters. These neural networks are referred to herein as relevance neural networks.

Figure 3:
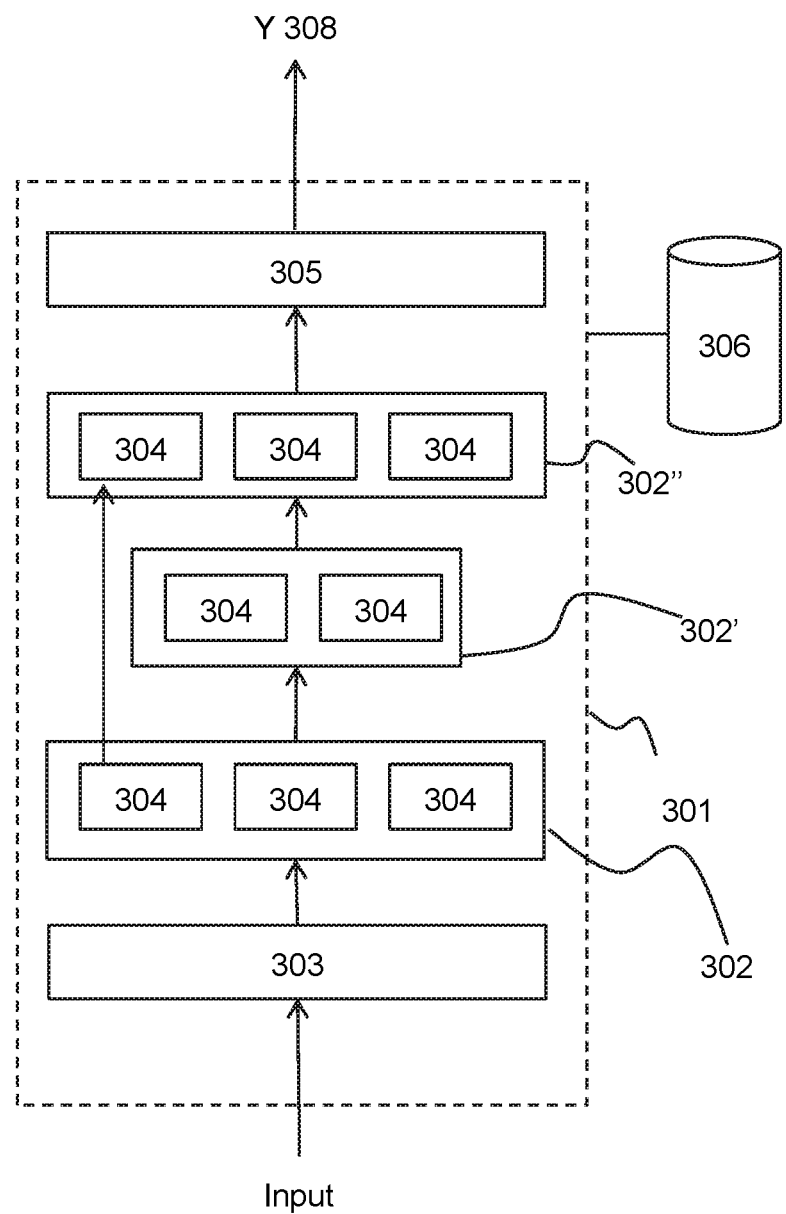
FIG. 3 is a block diagram of a relevance score neural network.

An exemplary relevance neural network is shown in FIG. 3. A relevance neural network (301) is a neural network comprising a layer of input values that represents the position-dependent tracks (303) (which may be referred to as an "input layer"), one or more layers of feature detectors (302, 302', 302'') and a layer of output values that represents the relevance scores (305) (which may be referred to as an "output layer"). Each layer of feature detectors (302, 302', 302'') comprises one or more feature detectors (304), wherein each feature detector comprises or is implemented by a processor. Weights may be applied in each feature detector (304) in accordance with learned weighting, which is generally learned in a training stage of the neural network. The input values, the learned weights, the feature detector outputs and the output values may be stored in a memory (306) linked to the relevance neural network (301).

It will be appreciated that relevance neural networks can be configured to produce a series of computations that implement other machine learning architectures, such as linear regression, logistic regression, decision trees and random forests. The position-dependent tracks may include DNA accessibility scores, nucleosome structure scores, RNA-secondary structure, protein secondary structure, tracks of common and rare mutations in human populations, retrovirus-induced repeats and evolutionary conservation scores.

In one embodiment, a relevance neural network that takes as its input a set of position-dependent tracks obtained with structural, biochemical, population and evolutionary data of biological sequences is used to determine the relevance scores. The relevance neural network determines the relevance scores using the values of the tracks at the position whose relevance score is being predicted:

$$r[i] \leftarrow f(u[i]; \theta),$$

where u[i] is a vector containing the structural, biochemical, population and evolutionary track values at position i in the sequence, and f is a neural network with parameters θ. There may be different relevance neural networks for different filters.

In another embodiment, the relevance neural network takes as input the values of the tracks within a window around the position whose relevance score is being predicted:

$$r[i] \leftarrow f(u[i-N:i+N]; \theta),$$

where u[i−N:i+N] comprises the structural, biochemical, population and evolutionary track values at positions i−N, i−N+1,i−N+2, ... , i+N−2,i+N−1,i+N in the sequence. For T tracks, u[i−N:i+N] is a T×(2N+1) matrix. It will be appreciated that other definitions of the window may be used.

In another aspect, the relevance neural network f(u[i]; θ) learns how a particular convolutional filter should ignore genomic sequences dependent on structural, biochemical, population and/or evolutionary information available to the predictor. Because the relevance predictor is shared among positions across the genome, it may be a statistically parsimonious model and information on how a convolutional filter should respond to biological sequences can be combined to produce statistically useful predictors.

In another aspect, the relevance neural networks may be applied not only to the lowest level convolutional filters that act on biological sequences, but also to intermediate-level convolutional filters that act on feature maps generated by lower-level convolutional filters. These intermediate-level convolutional filters may detect intermediate-level biological sequence features and have a receptive field with a size that depends on the size of the lower level convolutional filters and pooling layers. The relevance neural networks for intermediate-level convolutional filters can take as input the structural, biochemical, population and evolutionary relevance tracks within a window in the biological sequence fully or partially covering the receptive field of the convolutional filter.

In another embodiment, the MPCNN and the relevance neural network can be trained using a dataset consisting of biological sequences; tracks for structural, biochemical, population and evolutionary data; and MPCNN targets, such as molecular phenotypes. To adjust the parameters of the MPCNN and the relevance neural network, the architecture is operated in the back-propagation mode, which requires computing derivatives of the MPCNN output with respect to the intermediate computations, including outputs of the filters and the relevance scores, as well as the parameters of the MPCNN and the parameters of the relevance neural networks. This combined MPCNN-relevance neural network is fully differentiable and back-propagation may be used to compute the gradient of all parameters. Therefore, the system may be trained jointly with standard deep learning methods such as stochastic gradient descent so that the MPCNN and the relevance network work better together.

In this embodiment, the operation of the MPCNN in the back-propagation mode is modified so as to provide gradients that are used by the relevance neural network operating in the back-propagation mode. In particular, the gradient of the filter output with respect to the output of the relevance neural network is needed. For the embodiment wherein $$y[i] \leftarrow \sum_{k=-K}^{K} (r[i-k]s[i-k] + (1 - r[i-k])m)h[k],$$

the gradient is $$\left(\frac{\partial y[i]}{\partial r[i']}\right)^{mod} \leftarrow s([i'] - m)h[i - i'].$$

In another embodiment, biological sequences containing mutations can be fed into the MPCNN architecture and analyzed, using any of the following methods. 1) Re-determine the relevance score sequence taking into account the mutation. For example, if the relevance scores comprise secondary structure tracks determined using a secondary structure simulation system, the system can be used to determine the secondary structure track for the mutated sequence. 2) Set the relevance score in the location of the mutation to a value that is derived using other relevance scores, such as the average of the relevance scores in a window centered at the mutation. 3) Use the original relevance score sequence for the mutated sequence.

Figure 4:
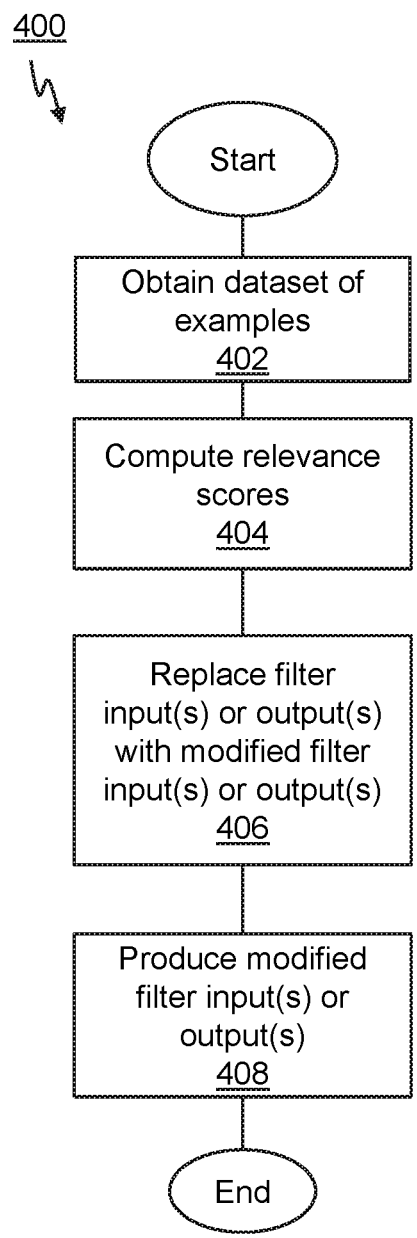
FIG. 4 illustrates an exemplary flowchart of a method for training CNNs using biological sequences and relevance scores.

Referring now to FIG. 4 an exemplary flowchart illustrates a method (400) for training MPCNNs using biological sequences and relevance scores. At block 402, a dataset of examples is obtained, wherein each example comprises a biological sequence encoded as a vector sequence, and one or more relevance score sequences derived from structural, biochemical, population, or evolutionary data. At block 404, relevance scores are either obtained or are computed using a relevance neural network for one or more positions in each biological sequence using data derived from structural, biochemical, population or evolutionary data. At block 406, one or more filter inputs are replaced with one or more modified filter inputs or one or more filter outputs are replaced with one or more modified filter outputs. At block 408, modified filter input(s) or output(s) are obtained. For each vector sequence and for one or more filters in the convolutional neural network, modified filter inputs or outputs are produced for the one or more positions by multiplying the respective filter inputs or outputs for the one or more positions by the relevance scores for the one or more positions. Alternatively, modified filter inputs are produced for the one or more positions by multiplying the filter inputs for the one or more positions by the relevance scores for the one or more positions and adding one minus the relevance scores for the one or more positions times a reference vector.

Although the invention has been described with reference to certain specific embodiments, various modifications thereof will be apparent to those skilled in the art without departing from the spirit and scope of the invention as outlined in the claims appended hereto.

The invention claimed is:

1. A system for weighting convolutional layers in a molecular phenotype convolutional neural network (MPCNN), the system comprising:
   a. the MPCNN comprising at least three layers, each of the at least three layers configured to receive inputs and produce outputs, a first layer of the at least three layers configured to obtain a biological sequence comprising a plurality of positions, a last layer of the at least three layers representing a molecular phenotype, each layer of the at least three layers other than the first layer configured to receive inputs from the produced outputs of one or more prior layers of the at least three layers;
   b. one or more of the at least three layers configured as convolutional layers, each of the convolutional layers comprising one or more convolutional filters linking the received inputs of the convolutional layer to produced outputs of the convolutional layer, the received inputs of the convolutional layer comprising a plurality of convolutional layer input positions, the produced outputs of the convolutional layer comprising a plurality of convolutional layer output positions; and
   c. one or more weighting units, each of the one or more weighting units linked to at least one of the one or more convolutional filters of a convolutional layer, each of the one or more weighting units associated with a relevance score sequence, each of the relevance score sequences comprising a plurality of relevance score sequence positions, each of the plurality of relevance score sequence positions associated with a numerical value, wherein the numerical value quantifies a biological relevance of a corresponding position in the biological sequence with respect to the at least one of the one or more convolutional filters of a convolutional layer, each of the one or more weighting units configured to use the associated relevance score sequence to weight operations of the associated convolutional filter of the one or more convolutional filters.

2. The system of claim 1, wherein at least one of the one or more weighting units is configured to use the associated relevance score sequence to weight the produced outputs of the associated convolutional layer.

3. The system of claim 1, wherein at least one of the one or more weighting units is configured to use the associated relevance score sequence to weight the received inputs of the associated convolutional layer.

4. The system of claim 1, wherein one or more of the at least three layers are configured as pooling layers, each of the pooling layers comprising a pooling unit linking received inputs of the pooling layer to produced outputs of the pooling layer, the received inputs of the pooling layer comprising a plurality of pooling layer input positions, the produced outputs of the pooling layer comprising a plurality of pooling layer output positions, wherein the received inputs of the pooling layer are linked to the produced outputs of at least one of the one or more convolutional layers.

5. The system of claim 1, wherein one or more of the at least three layers other than the first layer are configured as fully connected layers, wherein the produced outputs of each of the one or more fully connected layers are obtained at least in part by multiplying the received inputs of the fully connected layer by corresponding parameters to produce a plurality of products, determining a sum of the plurality of products, and applying a linear or a nonlinear function to the sum.

6. The system of claim 1, wherein the one or more relevance score sequences are obtained from evolutionary conservation sequences, population allele frequency sequences, nucleosome positioning sequences, ribonucleic acid (RNA)-secondary structure sequences, protein secondary structure sequences, or retroviral insertion sequences.

7. The system of claim 1, further comprising an encoder configured to encode the biological sequence as a vector sequence.

8. The system of claim 1, further comprising an MPCNN training unit configured to train the MPCNN using a plurality of training cases, each of the plurality of training cases comprising a biological sequence and a molecular phenotype.

9. The system of claim 1, further comprising a relevance score neural network configured to generate the one or more relevance score sequences.

10. The system of claim 9, further comprising a relevance score neural network training unit configured to train the relevance score neural network using a plurality of training cases, each of the plurality of training cases comprising a biological sequence and a relevance score sequence.

11. A method for weighting layers in a molecular phenotype convolutional neural network (MPCNN), the method comprising:
  a. obtaining the MPCNN comprising at least three layers, each of the at least three layers receiving inputs and producing outputs, a first layer of the at least three layers obtaining a biological sequence comprising a plurality of positions, a last layer of the at least three layers representing a molecular phenotype, each layer of the at least three layers other than the first layer receiving inputs from the produced outputs of one or more prior layers of the at least three layers, wherein one or more of the at least three layers are convolutional layers, each of the convolutional layers comprising one or more convolutional filters linking the received inputs of the convolutional layer to produced outputs of the convolutional layer, the received inputs of the convolutional layer comprising a plurality of convolutional layer input positions, the produced outputs of the convolutional layer comprising a plurality of convolutional layer output positions;
  b. obtaining one or more relevance score sequences, each of the one or more relevance score sequences comprising a plurality of relevance score sequence positions, each of the plurality of relevance score sequence positions associated with a numerical value, wherein the numerical value quantifies a biological relevance of a corresponding position in the biological sequence with resect to the at least one of the one or more convolutional filters of a convolutional layer; and
  c. applying one or more weighting operations, wherein each weighting operation of the one or more weighting operations comprises using an associated relevance score sequence in the one or more relevance score sequences to weight operations of an associated convolutional filter of the one or more convolutional filters.

12. The method of claim 11, wherein applying at least one of the one or more weighting operations comprises using the associated relevance score sequence to weight the produced outputs of the associated convolutional layer.

13. The method of claim 11, wherein applying at least one of the one or more weighting operations comprises using the associated relevance score sequence to weight the received inputs of the associated convolutional layer.

14. The method of claim 11, wherein one or more of the at least three layers are configured as pooling layers, each of the pooling layers performing a pooling operation to link the received inputs of the pooling layer to produced outputs of the pooling layer, the received inputs of the pooling layer comprising a plurality of pooling layer input positions, the produced outputs of the pooling layer comprising a plurality of pooling layer output positions, wherein the received inputs of the pooling layer are linked to the produced outputs of at least one of the one or more convolutional layers.

15. The method of claim 11, wherein one or more of the at least three layers other than the first layer are configured as fully connected layers, wherein the produced outputs of each of the one or more fully connected layers are obtained at least in part by multiplying the received inputs of the fully connected layer by corresponding parameters to produce a plurality of products, determining a sum of the plurality of products, and applying a linear or a nonlinear function to the sum.

16. The method of claim 11, wherein the one or more relevance score sequences are obtained from evolutionary conservation sequences, population allele frequency sequences, nucleosome positioning sequences, RNA-secondary structure sequences, protein secondary structure sequences, or retroviral insertion sequences.

17. The method of claim 11, further comprising performing an encoding operation that encodes the biological sequence as a vector sequence.

18. The method of claim 11, further comprising training the MPCNN using a plurality of training cases, each of the plurality of training cases comprising a biological sequence and a molecular phenotype.

19. The method of claim 11, further comprising generating the one or more relevance score sequences using a relevance score neural network.

20. The method of claim 19, further comprising training the relevance score neural network using a plurality of training cases, each of the plurality of training cases comprising a biological sequence and a relevance score sequence.

21. The system of claim 8, wherein training the MPCNN comprises adjusting parameters of the MPCNN using gradients of the parameters.

22. The system of claim 21, wherein adjusting parameters of the MPCNN comprises one or more of: a batch gradient descent, a stochastic gradient descent, a dropout, and a conjugate gradient method.

23. The system of claim 9, wherein the relevance score neural network comprises a fully connected neural network, a convolutional neural network, a multi-task neural network, a recurrent neural network, a long short-term memory neural network, an autoencoder, or a combination thereof.

24. The system of claim 10, wherein training the relevance score neural network comprises adjusting parameters of the relevance score neural network using gradients of the relevance score neural network.

25. The system of claim 24, wherein adjusting parameters of the relevance score neural network comprises one or more of: a batch gradient descent, a stochastic gradient descent, a dropout, and a conjugate gradient method.

26. The method of claim 18, wherein training the MPCNN comprises adjusting parameters of the MPCNN using gradients of the parameters.

27. The method of claim 26, wherein adjusting parameters of the MPCNN comprises one or more of: a batch gradient descent, a stochastic gradient descent, a dropout, and a conjugate gradient method.

28. The method of claim 19, wherein the relevance score neural network comprises a fully connected neural network, a convolutional neural network, a multi-task neural network, a recurrent neural network, a long short-term memory neural network, an autoencoder, or a combination thereof.

29. The method of claim 20, wherein training the relevance score neural network comprises adjusting parameters of the relevance score neural network using gradients of the relevance score neural network.

30. The method of claim 29, wherein adjusting parameters of the relevance score neural network comprises one or more of: a batch gradient descent, a stochastic gradient descent, a dropout, and a conjugate gradient method.

31. The method of claim 1, wherein the MPCNN outputs molecular phenotypes comprising numerical values which quantify aspects of biological molecules of cells.

32. The method of claim 11, wherein the MPCNN outputs molecular phenotypes comprising numerical values which quantify aspects of biological molecules of cells.

* * * * *

UNITED STATES PATENT AND TRADEMARK OFFICE
CERTIFICATE OF CORRECTION

PATENT NO. : 11,636,920 B2
APPLICATION NO. : 16/230149
DATED : April 25, 2023
INVENTOR(S) : Xiong et al.

Page 1 of 1

It is certified that error appears in the above-identified patent and that said Letters Patent is hereby corrected as shown below:

In the Claims

Claim 11, Line 40:
Replace "resect to the at least one of the one or more convolu-" with
--respect to the at least one of the one or more convolu- --.

Signed and Sealed this
Twenty-third Day of May, 2023

Katherine Kelly Vidal
*Director of the United States Patent and Trademark Office*